United States Patent [19]

Timmons et al.

[11] Patent Number: 4,808,160
[45] Date of Patent: Feb. 28, 1989

[54] NASAL CANNULA APPARATUS

[76] Inventors: John W. Timmons; Gloria A. Timmons, both of 8390 W. Country Club Dr., Sarasota, Fla. 33580

[21] Appl. No.: 927,525

[22] Filed: Nov. 5, 1986

Related U.S. Application Data

[63] Continuation-in-part of Ser. No. 851,209, Apr. 14, 1986, abandoned.

[51] Int. Cl.$^4$ .............................................. A61M 11/00
[52] U.S. Cl. ................................ 604/94; 128/207.18; 128/DIG. 26
[58] Field of Search ................................ 604/94, 179; 128/207.18, DIG. 26

[56] References Cited

U.S. PATENT DOCUMENTS

| | | | |
|---|---|---|---|
| 853,431 | 5/1907 | Allen | 128/207.18 |
| 2,168,705 | 10/1938 | Francisco et al. | 128/207.18 |
| 2,831,487 | 4/1958 | Tafilaw | 128/207.18 |
| 4,151,843 | 5/1979 | Brekke et al. | 128/207.18 |
| 4,406,283 | 9/1983 | Bir | 128/207.18 |
| 4,422,456 | 12/1983 | Tiep | 604/94 |
| 4,465,067 | 8/1984 | Koch et al. | 128/207.18 |
| 4,559,941 | 12/1985 | Timmons et al. | 128/207.18 |
| 4,641,647 | 2/1987 | Behan | 128/207.18 |
| 4,708,446 | 11/1987 | Timmons et al. | 128/207.18 |

Primary Examiner—John D. Yasko
Assistant Examiner—Gene B. Kartchner
Attorney, Agent, or Firm—Charles J. Prescott

[57] ABSTRACT

A nasal cannula apparatus supported by a headband is disclosed for use by sleeping and by those desiring a comfortable arrangement. A pair of cannula tubes, having a connection to a supply of the gas to be administered, is led to a cannula junction supported by a headband. One tube of the pair extends on each side of the head of the wearer. The cannula junction may be positioned within the headband where the headband is tubular. In this case the tubes would extend through the headband. At the cannula junction the tubes may merely be secured, or they may terminate to sockets in the junction. From the cannula junction the tubes, or new separable tube ends, descend on either side of the wearer's nose and against the wearer's face, as directed by grooves in the cannula junction. The tubes are then curved more than 180 degrees to provide a biased grip to the ala of the nostrils, and then recurve a lesser amount so that the tube ends are not against the nostril tissues.

21 Claims, 2 Drawing Sheets

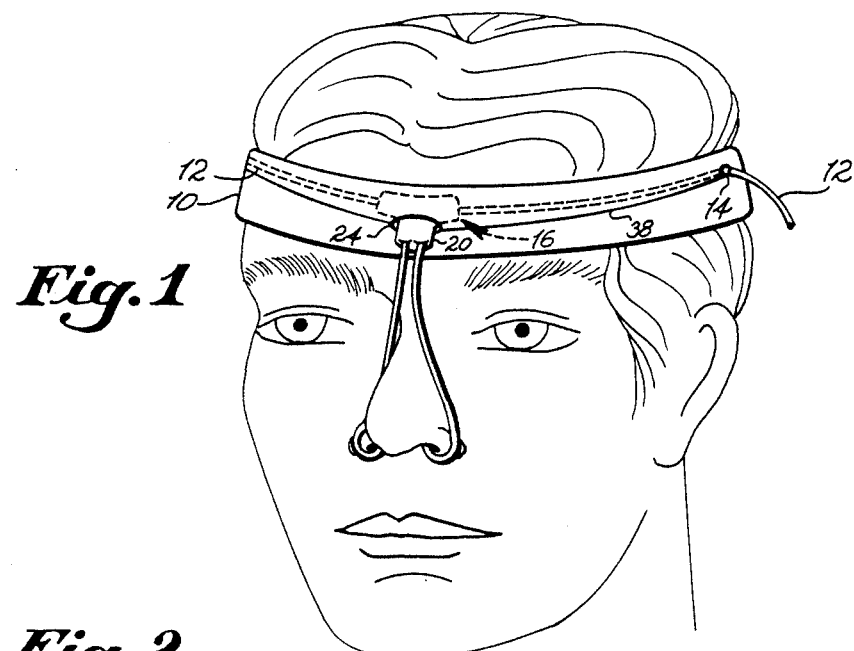
Fig. 1
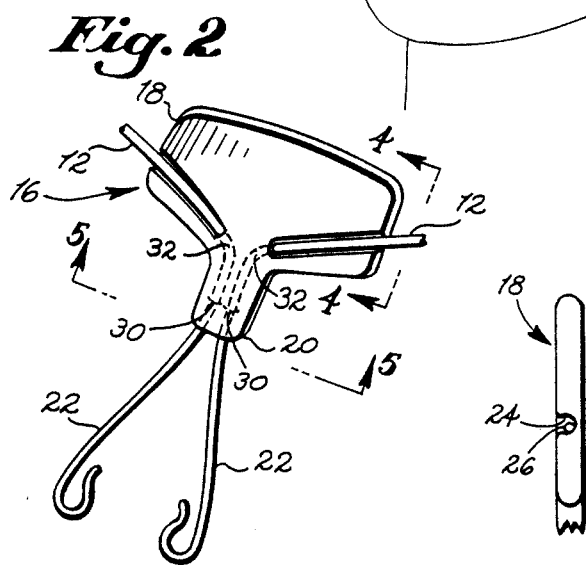
Fig. 2
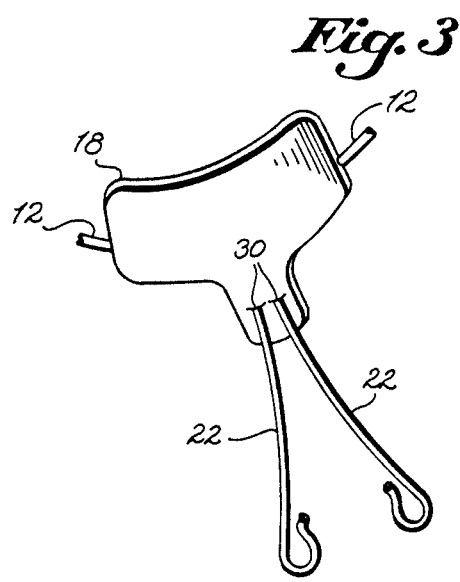
Fig. 3
Fig. 4
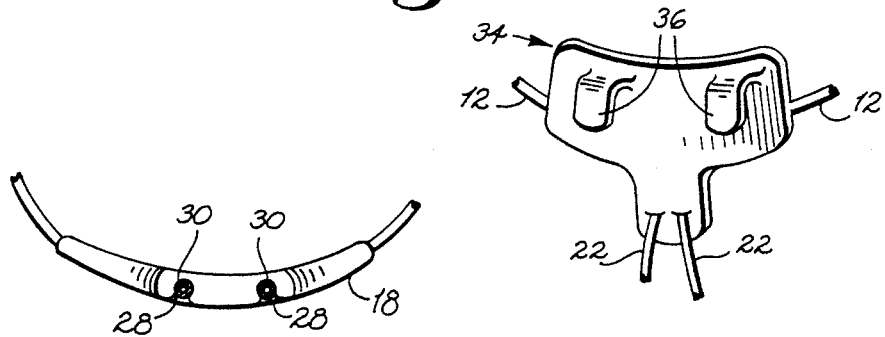
Fig. 5
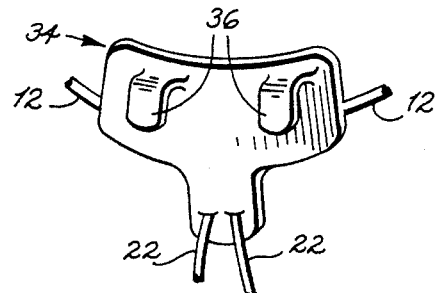
Fig. 6

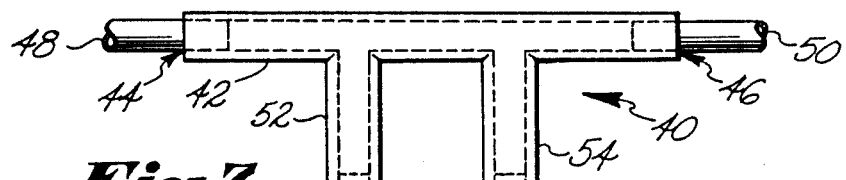
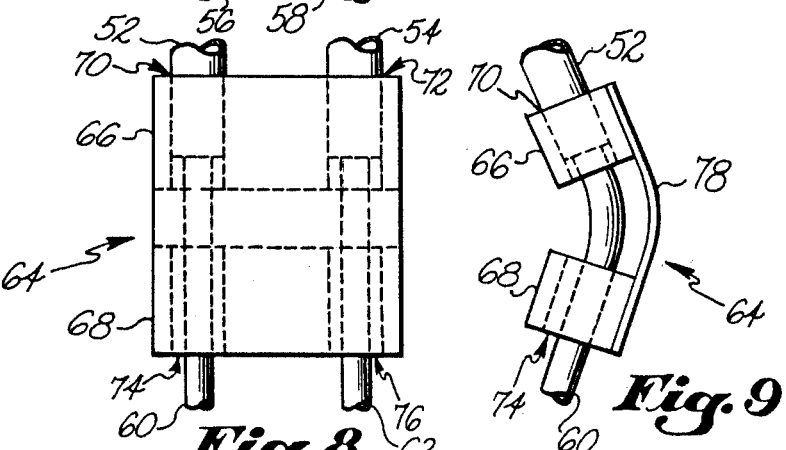
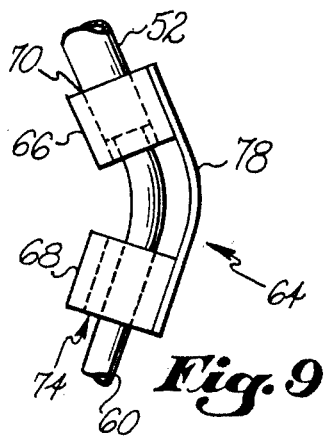
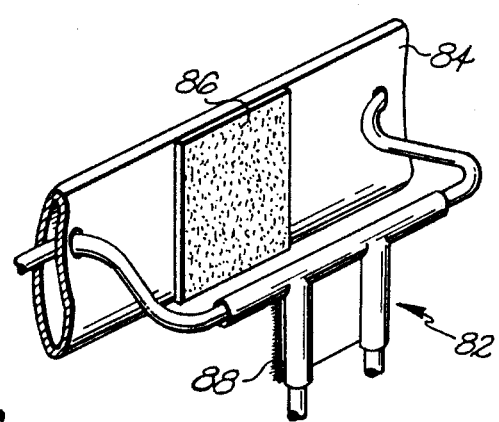
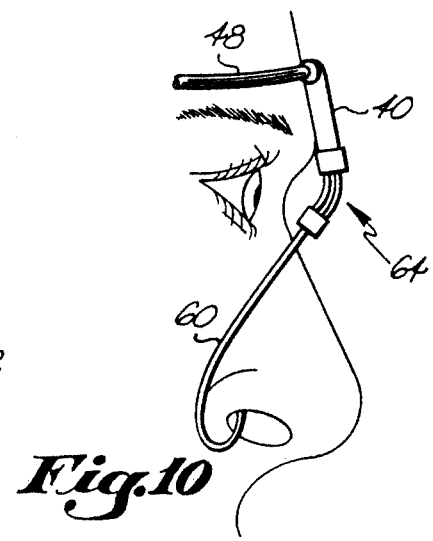
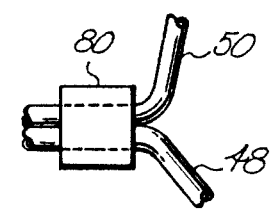
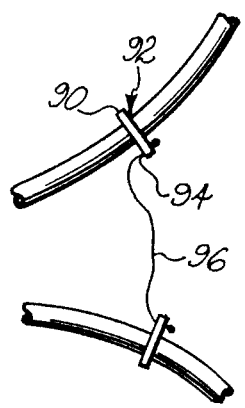
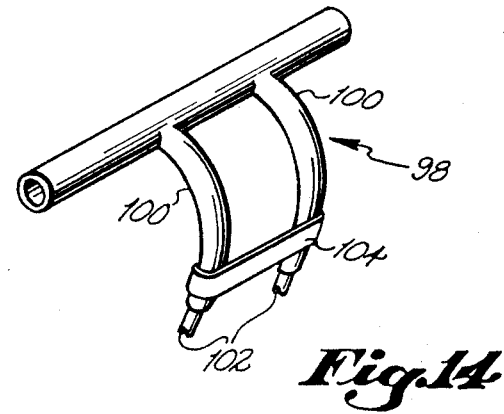

NASAL CANNULA APPARATUS

CROSS-REFERENCE TO RELATED APPLICATION

This application is a continuation-in-part of U.S. patent application Ser. No. 06/851,209, filed 4-14-86, entitled "Nasal Cannula Headband Apparatus" now abandoned.

BACKGROUND OF THE INVENTION

1. Field of the Invention

This invention relates generally to a nasal cannula apparatus, and more particularly to a comfortable and economical supporting arrangement for such apparatus.

2. Description of Related Art

People requiring the administration of a gas such as oxygen for extended times us cannula apparatus which delivers the gas through tubes to each nostril.

U.S. Pat. No. 4,559,941, Timmons et al., entitled "Eyeglass Frame and Nasal Cannula Assembly", discloses a cannula apparatus which supports and substantially conceals the cannula tubes by eyeglass frames. That arrangement is not well suited for use while the wearer is sleeping. In addition, some individuals who do not wear glasses for reasons of vision, find glasses uncomfortable or awkward and would prefer another nasal cannula arrangement.

U.S. Pat. No. 2,168,705, Francisco et al., entitled "Nasal Inhaler", discloses a support for cannula tubes having temples which clasp behind the wearer's ears and include nose pads of the type used with eyeglasses. The use of temples and nose pads also makes this arrangement not well suited for use while the wearer is sleeping.

U.S. Pat. No. 2,259,817, Hawkins, entitled "Adjustable Head Attachment for Oxygen Tubes" discloses a support for cannula tubes having an adjustable temple band and an adjustable crown band. These bands and associated buckles, together with the obtrusive nose portion of the cannula tube also make this arrangement unsuitable for sleeping.

U.S. Pat. No. 3,726,275, Jackson et al., entitled "Nasal Cannulae", discloses an arrangement in which the cannula tubes are looped or draped over the ears of the wearer and coupled under the chin with a ring slide. This arrangement appears to be easily dislodged when the wearer is not standing erect and also appears unsuitable for sleeping.

SUMMARY OF THE INVENTION

A nasal cannula apparatus is provided having a cannula junction to which the cannula tubes from the supply are led. Nasal extensions connected to the cannula junction lead to the nostrils of the wearer. The cannula junction is positioned on the forehead of the wearer and in one embodiment has an elasticized headband as a support. The headband is made of soft material such as terry cloth in tubular form. The cannula tubes have a portion enclosed in the tubular headband, entering at the rear and extending, one on each side, to the cannula junction at the front. The cannula junction not only supports the separable nasal extensions, but also positions them properly.

In another embodiment, the cannula junction is adapted to be attached to a separate headband.

It is therefore an object of this invention to provide a nasal cannula headband apparatus which will securely and comfortably hold nasal cannula tubes.

It is a further object of this invention to provide a nasal cannula headband apparatus which permit separable cannula nasal end tubes or extensions to be connected and disconnected.

It is also an object of this invention to provide nasal cannula headband apparatus which will properly position cannula nasal end tubes.

In accordance with these and other objects which will become apparent hereinafter, the instant invention will not be described with reference to the accompanying drawings.

BRIEF DESCRIPTION OF THE DRAWINGS

FIG. 1 is a three-quarter front elevation of the apparatus of this invention in place on a wearer;

FIG. 2 is a front elevation of the cannula junction of the apparatus of FIG. 1;

FIG. 3 is a rear elevation of the cannula junction of the apparatus of FIG. 1;

FIG. 4 is an enlarged detail of the cannula junction of FIG. 2 in the direction of arrows 4—4 on FIG. 2;

FIG. 5 is an enlarged detail of the cannula junction of FIG. 2 in the direction of arrows 5—5 on FIG. 2;

FIG. 6 is an alternate embodiment of the cannula junction;

FIG. 7 is an alternate embodiment of the cannula junction;

FIG. 8 is a front elevation of a biasing device for use with the apparatus;

FIG. 9 is a side elevation of the biasing device of FIG. 8;

FIG. 10 is a side elevation showing the cannula junction and biasing device in use;

FIG. 11 shows a fastening arrangement for cannula tubes;

FIG. 12 shows an alternate way of positioning a cannula junction on a headband;

FIG. 13 shows an alternate fastening arrangement for cannula tubes; and

FIG. 14 is an alternate embodiment of a cannula junction.

DETAILED DESCRIPTION OF THE INVENTION

Referring to FIG. 1, headband 10 is fabricated in tubular form and contains within the tubular headband, on each side of the wearer's head, a headband cannula tube 12. Each of the two headband cannula tubes 12 enter headband 10 near the back of the wearer's through an opening 14 in headband 10. The pair of headband cannula tubes 12 extend through headband 10 to the front portion thereof. At the center of the front portion of headband 10, and also contained within the tubular folds thereof, is positioned cannula junction 16. Headband cannula tubes 12 are held by cannula junction 16.

Referring to FIG. 2, cannula junction 16 is shown in more detail. Cannula junction 16 has a laterally extending junction support plate 18, and a more narrow, vertical extension 20. Headband cannula tubes 12 are located on the outwardly (with respect to the wearer) facing portion of junction support plate 18. Cannula nasal extensions 22 are located on the inwardly facing portion of nasal extension 20 of cannula junction 16. Cannula junction 16 may be made of a pliable and permanently deformable material so that it may be adjusted to conform to different forehead shapes and wearing positions.

Returning to FIG. 1, vertical extension 20 of cannula junction 16 is seen to extend through opening 24 in headband 10. Opening 24 and openings 14, together with cannula junction 16, with its junction support plate 18 and vertical extension 20, serve to maintain junction support plate 18 in position at the center of the front portion of headband 10.

Headband 10 is preferably fabricated of a soft material such as terry cloth and is also somewhat elasticized. Such headbands are commercially available and known as sweat bands. Headband 10 may be about one inch or more wide to provide a bearing surface against the head of the wearer which will distribute the slight tension of the elasticized material so as to avoid discomfort to the wearer, even if the nasal headband cannula apparatus is worn for prolonged periods, such as through the night. Headband cannula tubes 12 are not held in position within headband 10 except by cannula junction 16. This permits headband cannula tubes 12 to have greater or lesser lengths within headband 10 to accommodate for wearers having heads of different sizes. In other words, one size fits all, within reason. The two headband cannula tubes 12 may be connected to a single tube which supplies the oxygen or other gas in the conventional manner.

Turning now to FIGS. 2-5, cannula junction plate 18 may have a slight curvature, as shown most clearly in FIG. 5. Cannula junction plate 18 is shown as being a unitary body, and a molded unitary body may be the most convenient manner to provide this component. However, it may also be an assembly of two or more parts. Of more importance in carrying out the invention is the provision of a mechanically secure connection and a substantially airtight passage between headband cannula tubes 12 and cannula nasal extensions 22. One way of providing the substantially airtight passage is to make cannula nasal extensions 22 a unitary part of headband cannula tubes. That is, the same tubes connected to the gas supply may terminate in the nostrils of the wearer, with cannula junction 16 holding the tubes in place. This way is not preferred because the cannula nasal extensions require replacement more often than the headband cannula tubes. Such more often replacement may occur when one person uses the apparatus over an extended time, or when multiple persons use the apparatus for shorter times. Nevertheless, cannula junction 16 may serve to hold continuous tubes in place. (The previously referred to U.S. Pat. No. 4,708,446, provides an extensive description of the advantages of separable cannula nasal extensions.)

FIG. 4 shows an end view of junction support plate 18 with headband cannula tube 12 removed. Groove 24 extends from the edge of junction support plate 18 in to socket 26 (also shown in FIG. 2). Groove 24 is undercut to securely hold headband cannula tube 12.

FIG. 5 shows an end view of vertical extension 20 of cannula junction 16 with separable cannula nasal extensions 22 removed. Grooves 28 extend from the bottom of vertical extension 20 up to sockets 30 (also shown in FIGS. 2 and 3). Grooves 28 are undercut to securely hold cannula nasal extensions 22.

As indicated previously, the preferred embodiment uses separable, and consequently replaceable, cannula nasal extensions 22; and in this embodiment the ends of cannula nasal extensions 22 are plugged into sockets 30 and the adjacent tubes snapped into grooves 28. Similarly, the ends of headband cannula tubes 12 are plugged into sockets 26 and the adjacent tubes snapped into grooves 24. Cannula junction 16 provides airtight passages 32 between sockets 26 and 30.

If it is desired to use continuous tubes between the gas supply line and the nostrils of the wearer, passages 32 need not be airtight, but grooves or the like are needed to securely hold the tubes so that the tubes will not freely slide.

Although headband 10 is shown in FIG. 1 with only openings 14 and 24, it may be desired to permit headband to be opened to remove the cannula tubes and cannula junction. This may be done by making tubular headband 10 with a closure 38 extending from openings 14 to opening 24. Such a closure can be temporarily closed using snaps, Velcro type material, etc. This arrangement permits removal of the cannula apparatus to provide a new headband or even to launder the existing headband.

An alternate embodiment of the invention is illustrated in FIG. 6. Cannula junction 34 is identical to the cannula junctions described above except that it includes hook-shaped elements 36. Hook-shaped elements permit the attachment of cannula junction to an ordinary headband which has not been specifically fabricated for the cannula apparatus by hooking it over the top edge of the headband. The attaching arrangement may be of any other convenient form, for example, the hook-shaped elements can be the type used on Velcro material and be adhesively attached to cannula junction 34.

Turning to FIG. 7, cannula junction 40 is shown having a horizontally extending hollow member 42 with laterally oriented inlets 44 and 46. These inlets 44 and 46 receive cannula tubs 48 and 50, respectively. Cannula junction 40 also has laterally spaced hollow members 52 and 54, having downwardly oriented outlets 56 and 58, respectively. Outlets 56 and 58 receive nasal extensions 60 and 62 which are preferably of the type shown in FIG. 2, identified as 22.

As shown in FIG. 10, cannula junction 40 is positioned at the forehead of the wearer. The typical slope of the forehead does not orient outlets 56 and 58 (FIG. 7) of cannula junction 40 towards the nostrils of the wearer. Biasing device 64 is therefore provided to direct the nasal extensions, such as nasal extension 60 towards the nostrils and against the face of the wearer. Since the nasal extensions are made of flexible plastic, they will also follow the contours of the face once they are properly directed.

FIGS. 8 and 9 show biasing device 64 more clearly. Upper grip 66 and lower grip 68 are blocks having parallel passages 70 and 72, in upper grip 66, and 74 and 76 in lower grip 68. Passages 70-76 may be drilled or molded into blocks 66 and 68, and have an outer diameter large enough to accomodate hollow members 52 and 54 of cannula junction 40. Connecting upper grip 66 and lower grip 68 is arcuate member 78 which holds upper grip 66 and lower grip 68 at an angle to each other. Obviously, upper grip 66, lower grip 68 and arcuate member 78 may all be formed as a single component. Also, lower grip 68 may be formed of two separate blocks—each having a passage—and arcuate member 78 may connect these separate lower blocks to the upper grip without connecting the separate lower blocks to each other. This permits the nasal extensions to more easily spread apart.

It will be observed that passages 70-76 have a noticeably larger inside diameter than the outside diameter of nasal extensions 60 and 62. Because the passages 70 and 72 of the upper grip 66 are not aligned with the passages 74 and 76 of the lower grip 68, passages 74 and 76 will, never-the-less, properly direct nasal extensions 60 and 62. In fact, upper grip 66 and lower grip 68 may both be positioned on nasal extensions 60 and 62.

Returning to FIG. 10, it will be noted that no headband is shown. Cannula junction 40 may also be held in position at the forehead of the wearer by drawing cannula tubes 48 and 50 together at the back of the wearer's head as shown in FIG. 11, where a simple ring or cylinder 80 is used. This elemental apparatus is especially suitable where the various components will be used for a relatively short time and then discarded. Since all of the elements may be inexpensively be fabricated this elemental apparatus serves this function adequately.

FIG. 12 illustrates another alternate embodiment for the headband apparatus. Instead of positioning cannula junction 82 within headband 84, it may be adjustably positioned on the outside of headband 84. A vertical strip of releasable fastening material 86 is secured to the outside of headband 84. A complementary section of releasably fastening material 88 is secured to cannula junction 82. Thus cannula junction 82 may be secured to headband 84 in a desired vertical position. This vertical adjustability is desirable because the distance from the forehead to the nostrils varies. Vertical adjustment is possible by moving the headband and by moving the position of the cannula junction on the headband.

Referring to FIG. 13, a preferred method of securing cannula tubes on the head of a wearer when no headband is used is illustrated. Plate 90 which may be formed from a thin plastic sheet, has a first passage 92 for a cannula tube, and a second passage 94 for an elastic 96. Elastic 96 is passed through passage 94 and a knot formed to hold it from slipping back through passage 94. A similar arrangement is provided for the other cannula tube. The plate 90 may be moved along the cannula tube to a desired location in which the cannula junction will be centered on the forehead of the wearer and sufficient tension is applied by elastic 96. Any tendency for the cannula junction to move to one side or the other is resisted by the cannula tube and elastic arrangement.

In FIG. 14 an alternate cannula junction 98 is portrayed which is molded so that extensions 100 have an arcuate shape which will bias nasal extensions 102 against the face of the wearer. A lower horizontal support 104 is shown in this embodiment, however, horizontal support may be unnecessary with a sufficiently rigid material.

While the instant invention has been shown and described herein in what are conceived to be the most practical and preferred embodiments, it is recognized that departures may be made therefrom within the scope of the invention, which is therefore not to be limited to the details disclosed herein but is to be accorded the full scope of the claims so as to embrace any and all equivalent apparatus and articles.

We claim:

1. A nasal cannula apparatus for receiving a gas from a supply line and delivering it to the nostrils of a wearer comprising:
    a pair of cannula tubes having ends;
    a pair of nasal extensions;
    a cannula junction;
    said cannula junction having first and second laterally oriented and oppositely directed inlets for receiving and holding said pair of cannula tube ends;
    said cannula junction also having first and second laterally spaced, downwardly oriented, outlets for receiving and holding said pair of nasal extensions, where by said nasal extensions may be readily replaced without replacement of said cannula tubes; and
    support means for holding said cannula junction at the forehead of the wearer.

2. A nasal cannula apparatus in accordance with claim 1 further including:
    a nasal extension biasing device;
    said nasal extension biasing device having an upper grip and a lower grip with an intermediate arcuate member holding said upper grip and said lower grip, and directing said nasal extensions in a bifurcated fashion to lie against the face and on either side of the nose of the wearer.

3. A nasal cannula headband apparatus in accordance with claim 1 wherein:
    said support means for holding said cannula junction at the forehead of the wearer is an elasticized headband of soft material;
    said headband having a front portion and a rear portion;
    said cannula junction positioned at said front portion of said headband;
    said pair of cannula tubes connected to said supply line and extending, one at each side of said headband to said cannula junction; and
    said unconnected ends of each of said nasal extensions terminating in a first curved portion of more than 180 degrees, whereby said first curved portion will provide a spring biased gripping of the alae of the nostrils of the wearer.

4. A nasal cannula apparatus in accordance with claim 3 wherein: said headband is tubular.

5. A nasal cannula apparatus in accordance with claim 4 wherein:
    said cannula junction is positioned within said tubular headband;
    said pair of cannula tubes enter said tubular headband at said rear portion of said headband; and
    extend through said tubular headband to said cannula junction.

6. A nasal cannula apparatus in accordance with claim 4 wherein:
    said headband has a vertical strip of a releasable fastening material at said front portion of said headband; and
    said cannula junction has a section of a complementary releasable fastening material secured thereto, whereby said cannula junction may be secured to said headband at a desired vertical position.

7. A nasal cannula apparatus in accordance with claim 3 wherein:
    said unconnected ends of each of said cannula tubes have a second curved portion of a lesser amount than 180 degrees, whereby said second curved portion will space the end of said tube from the nostril tissues.

8. A nasal cannula apparatus in accordance with claim 1 wherein:
    said cannula junction has retaining grooves to receive and hold said cannula tubes.

9. A nasal cannula apparatus in accordance with claim 3 wherein:
said cannula junction includes a support plate portion extending laterally from both sides of said cannula junction.

10. A nasal cannula apparatus in accordance with claim 3 wherein:
said cannula junction includes a nasal extension portion extending downwardly from said cannula junction.

11. A nasal cannula apparatus in accordance with claim 10 wherein:
said center of said front portion of said headband has an opening; and
said nasal extension of said cannula junction extends through said opening.

12. A nasal cannula apparatus in accordance with claim 11 wherein:
said headband has two openings at said rear portion; and
a closure extends from said two openings at said rear portion to said opening in said center of said front portion, whereby said closure may be opened to remove said cannula apparatus from said headband.

13. A nasal cannula apparatus in accordance with claim 3 wherein:
said cannula junction has attaching means for attaching it to said headband.

14. A nasal cannula apparatus in accordance with claim 3 wherein:
said means for attaching said cannula junction is a plurality of hook shaped elements.

15. A nasal cannula apparatus for receiving a gas from a supply line and delivering it to the nostrils of a wearer comprising:
a cannula junction having a pair of inlets for receiving one end of a pair of cannula tubes having the other end connected to said supply line;
positioning means for positioning said cannula junction at the forehead of the wearer;
said cannula junction having a pair of outlets for receiving one end of a pair of nasal extensions, whereby said nasal extensions may be readily fixedly or replaceably inserted in said outlets; and
biasing means associated with said cannula junction means for directing said pair of nasal extensions in said outlets in a bifurcated fashion to lie against the face of and on either side of the nose of a wearer.

16. A nasal cannula apparatus in accordance with claim 15 wherein:
said cannula junction has undercut grooves to receive and hold said cannula tubes.

17. A nasal cannula apparatus in accordance with claim 16 wherein:
said cannula junction includes a support plate portion extending laterally from both sides of said cannula junction; and
said cannula junction includes a vertical extension portion extending downwardly from said cannula junction.

18. A nasal cannula headband apparatus for receiving a gas from a supply line and delivering it to the nostrils of a wearer comprising:
a tubular headband of soft material;
said headband being elasticized to accommodate for extension without producing excessive tension;
said headband having a bearing surface sufficient to spread the force due to said tension to avoid discomfort over a prolonged period of use;
said headband portion having a front portion and a center on said front portion;
a pair of cannula tubes;
each of said cannula tubes having a permanent headband portion enclosed in said headband and a separable nasal extension;
said permanent headband portion of said cannula tubes having a first end for connecting to said supply line of gas, and a second end;
said nasal extension having a connecting end and a nasal end;
a cannula junction;
said cannula junction receiving and maintaining in place said second end of said permanent headband portion of said cannula tubes;
said cannula junction receiving and maintaining in place said connecting ends of said cannula nasal extensions; and
said cannula junction directing said cannula nasal extensions in a bifurcated fashion to lie on either side of the wearer's nose and against the face.

19. A nasal cannula headband apparatus in accordance with claim 18 further including:
support means for holding said cannula junction on said headband.

20. A nasal cannula headband apparatus in accordance with claim 19 wherein:
said support means is a vertical strip of releasable fastening material connected to said headband; and
a section of complementary releasable fastening material connected to said cannula junction.

21. A nasal cannula headband apparatus for receiving a gas from a supply line and delivering it to the nostrils of a wearer comprising:
a pair of cannula tubes having first ends for connecting to the supply line and second ends;
a pair of nasal extensions having first ends for insertion in the nostrils of a wearer and second ends;
a cannula junction having first and second laterally oriented and oppositely directed inlets in which said second ends of said cannula tubes are fixedly secured; and
said cannula junction also having first and second laterally spaced and downwardly oriented outlets in which said second ends of said nasal extensions are fixedly secured.

* * * * *